(12) United States Patent
Mahaffey et al.

(10) Patent No.: US 8,636,749 B2
(45) Date of Patent: Jan. 28, 2014

(54) DERMATOME BLADE ASSEMBLY GUARD

(75) Inventors: Mark Mahaffey, New Philadelphia, OH (US); Bruce Straslicka, Medina, OH (US)

(73) Assignee: Zimmer Surgical, Inc., Dover, OH (US)

( * ) Notice: Subject to any disclaimer, the term of this patent is extended or adjusted under 35 U.S.C. 154(b) by 72 days.

(21) Appl. No.: 13/180,977

(22) Filed: Jul. 12, 2011

(65) Prior Publication Data

US 2013/0018391 A1    Jan. 17, 2013

(51) Int. Cl.
*A61B 17/50* (2006.01)
(52) U.S. Cl.
USPC .......................................... 606/132
(58) Field of Classification Search
USPC ............. 30/32, 50, 51, 52, 53, 54, 55, 57, 58, 30/59, 60, 60.5, 61, 62, 63, 64, 65, 77, 78, 30/79, 80, 81, 82, 83, 329, 337, 339, 340, 30/342; 606/131, 132, 133
See application file for complete search history.

(56) References Cited

U.S. PATENT DOCUMENTS

| | | |
|---|---|---|
| 2,457,772 A | 12/1948 | Barron et al. |
| 3,428,045 A | 2/1969 | Kratzsch |
| 3,583,403 A | 6/1971 | Keller |
| 3,670,734 A | 6/1972 | Hardy |
| 3,820,543 A | 6/1974 | Vanjushin |
| 3,857,178 A | 12/1974 | Stevens |
| 4,038,986 A | 8/1977 | Mahler |
| 4,098,278 A | 7/1978 | Schwartz |
| 4,257,160 A * | 3/1981 | Murai ............................. 30/41 |
| 4,754,756 A | 7/1988 | Shelanski |
| 4,917,086 A | 4/1990 | Feltovich |
| 5,873,881 A | 2/1999 | McEwen et al. |
| 2005/0101972 A1 | 5/2005 | Bhatavadekar et al. |
| 2006/0185490 A1 | 8/2006 | Mincer |
| 2009/0157095 A1 | 6/2009 | Barker et al. |
| 2009/0157096 A1 | 6/2009 | Boles |

OTHER PUBLICATIONS

Dictionary.com "cover" as accessed on Jun. 12, 2013; http://dictionary.reference.com/browse/cover.*

* cited by examiner

*Primary Examiner* — Ryan Severson
*Assistant Examiner* — Jonathan W Miles
(74) *Attorney, Agent, or Firm* — Seager, Tufte & Wickhem, LLC (57) ABSTRACT

A dermatome having a main body, a blade assembly and a blade guard, where the blade assembly has a blade edge and the blade guard has a base and a fence extending from the base toward the blade assembly so as to face the blade edge. The blade guard may include at least one blade assembly locator to facilitate the alignment of the blade guard with the blade assembly. A blade guard assembled on the blade assembly may operate so as to prevent unintended contact between the blade edge and objects.

17 Claims, 10 Drawing Sheets

DERMATOME BLADE ASSEMBLY GUARD

TECHNICAL FIELD

The disclosure is directed to dermatomes for surgically harvesting grafts of skin. More particularly, the disclosure is directed to protective guard assemblies for dermatome blade assemblies.

BACKGROUND

Conventional dermatomes are used for cutting skin tissue to obtain transplantable skin grafts. A skin graft is a patch of healthy skin that is harvested from one area of the body or donor site to cover a damaged or skinless area of the body. Typically, a dermatome has a front end holding a flat blade to be placed in contact with a tissue surface and a motor to oscillate the blade from side to side to create a slicing action which cuts the tissue as the dermatome is moved along the tissue surface.

SUMMARY

The disclosure is directed to several alternative designs, materials and methods of manufacturing medical device structures and assemblies. Although it is noted that conventional dermatomes exist, there exists a need for improvement on those devices.

Accordingly, one illustrative embodiment of the disclosure may include a dermatome having a blade assembly and a blade guard. The blade assembly may have a blade edge and the blade guard may include a fence extending from a base, where the fence may be configured to cover the blade edge. The blade guard may include at least one locator mechanism extending from the base in a similar direction as the fence, where the locator may be configured to communicate with the blade assembly and orient the blade guard with respect to the blade assembly. The attached blade assembly and blade guard may be mounted on a main body of a dermatome, after which the blade guard may be removed. At the same or another time, the blade guard may be reconnected to the blade assembly and the connected blade guard and blade assembly may be removed from the dermatome. Use of the blade guard may allow for handling of a blade assembly without the risk of an object coming into unintended contact with the blade edge.

The above summary of some example embodiments is not intended to describe each disclosed embodiment or every implementation of the disclosure.

DESCRIPTION OF THE DRAWINGS

The disclosure may be more completely understood in consideration of the following detailed description of various embodiments in connection with the accompanying drawings, in which.

While the disclosure is amenable to various modifications and alternative forms, specifics thereof have been shown by way of example in the drawings and will be described in detail. It should be understood, however, that the intention is not to limit aspects of the claimed disclosure to the particular embodiments described. On the contrary, the intention is to cover all modifications, equivalents, and alternatives falling within the spirit and scope of the claimed disclosure.

DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the claimed disclosure. The illustrative embodiments depicted are intended only as exemplary. Selected features of any illustrative embodiment may be incorporated into an additional embodiment unless clearly stated to the contrary.

The present disclosure relates to the subject matter filed by inventors Mark Mahaffey and Bruce Straslicka and contained in the U.S. patent application titled DERMATOME BLADE ASSEMBLY having Ser. No. 13/180,831 and the U.S. patent application titled DERMATOME WITH WIDTH PLATE CAPTURES having Ser. No. 13/180,925, both filed on Jul. 12, 2011, and which are both expressly incorporated herein by reference in their entirety.

Figure 6:
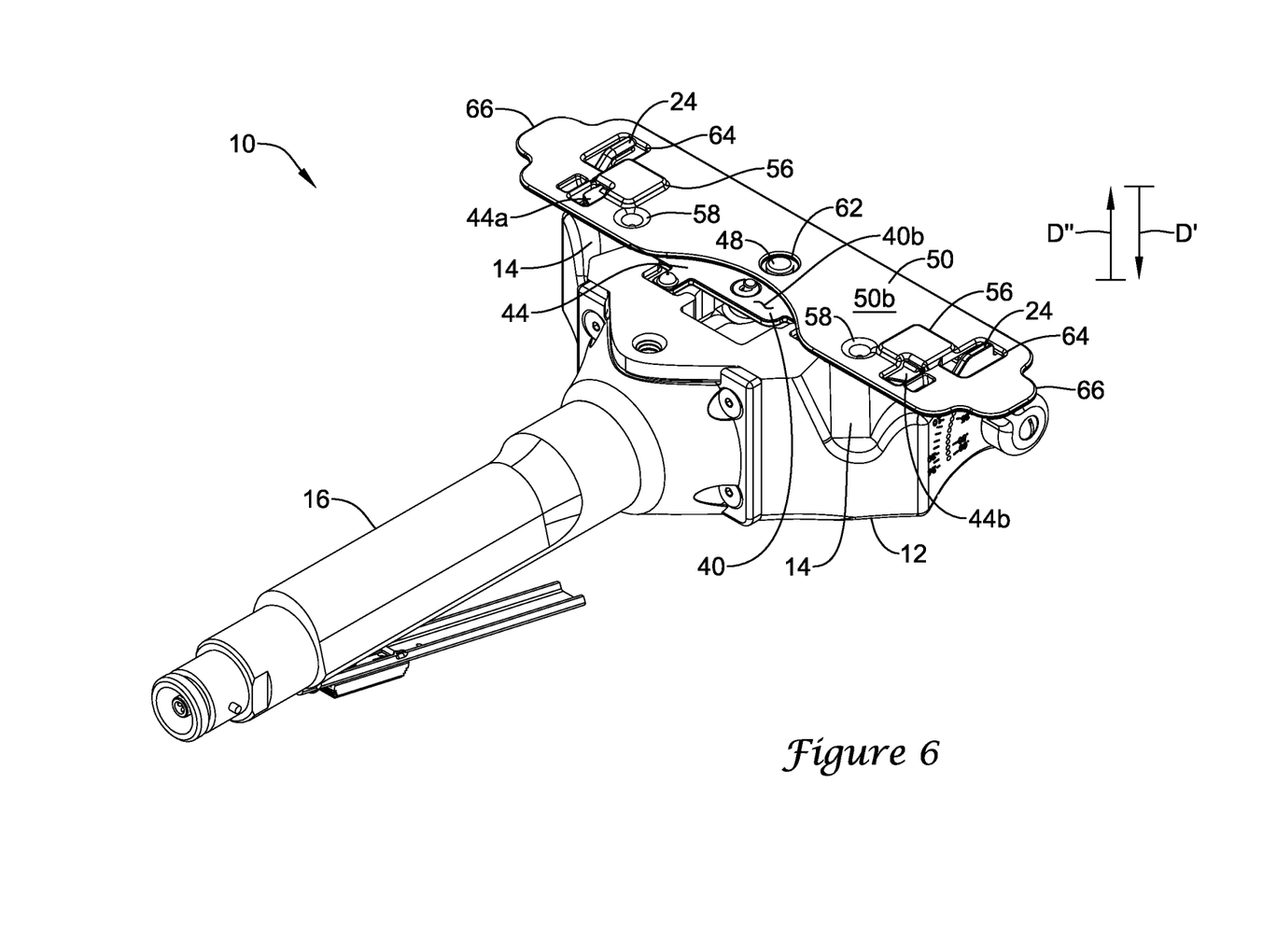
FIG. 6 is a bottom perspective view of features of a dermatome according to an aspect of the disclosure.
Figure 7:
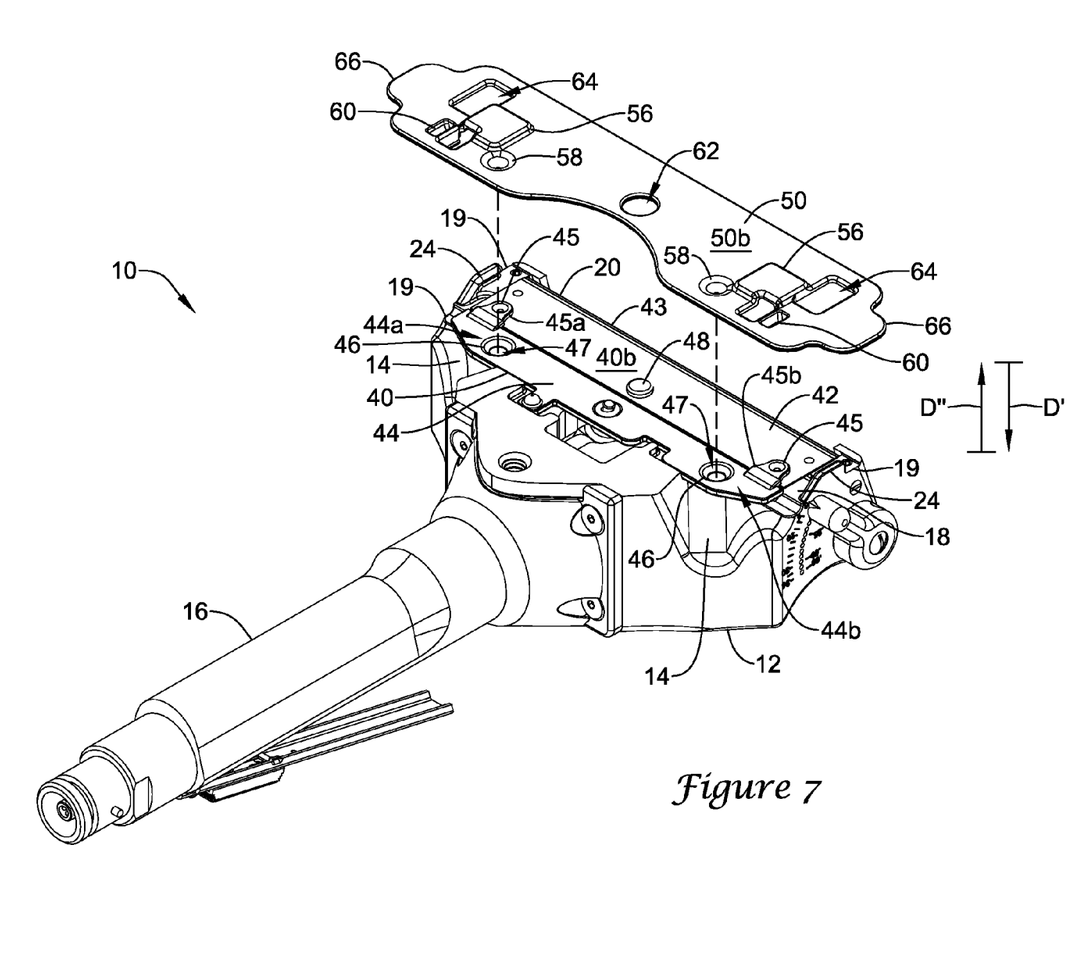
FIG. 7 is a partial exploded perspective view of features of a dermatome according to an aspect of the disclosure.
Figure 8:
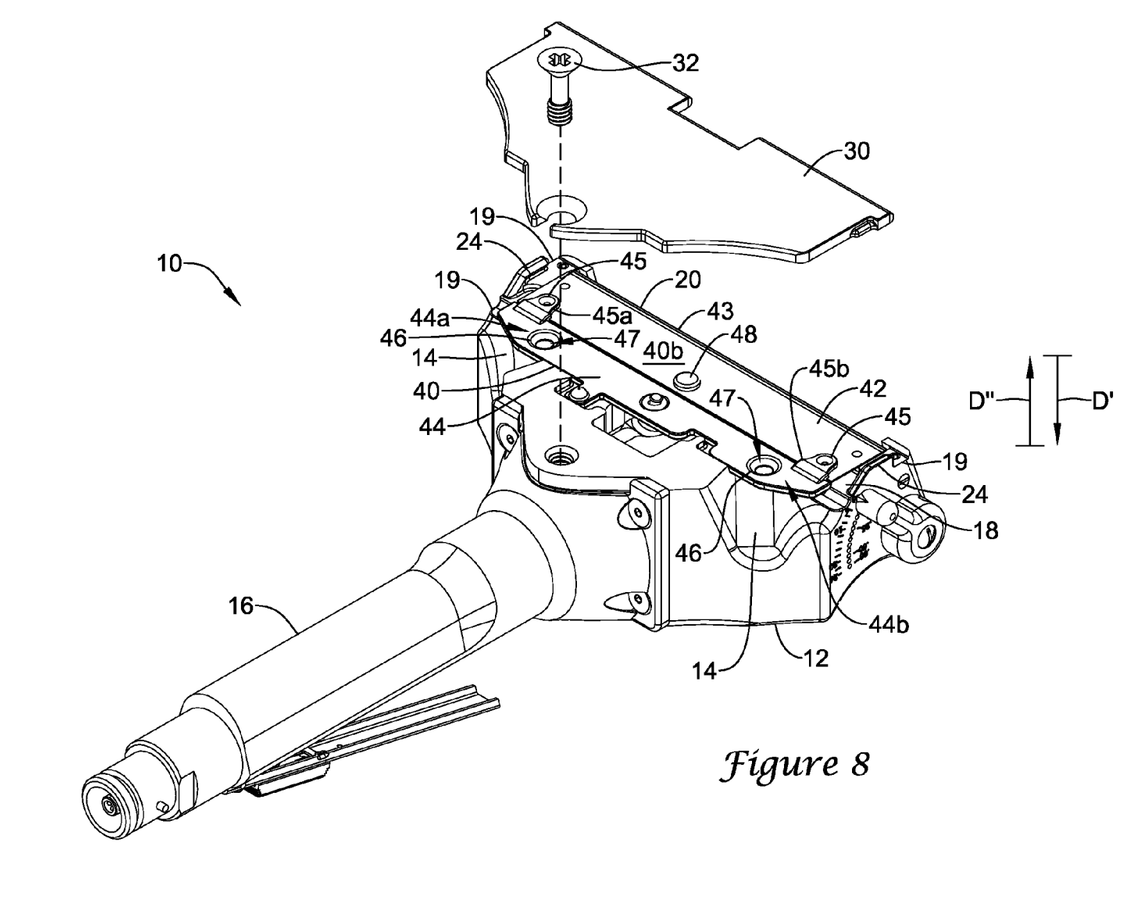
FIG. 8 is a partial exploded perspective view of features of a dermatome according to an aspect of the disclosure.

Referring to the Figures, dermatome 10 for harvesting grafts of skin tissue has a main body 12 connected to a handle 16, as seen in FIGS. 6-8. Dermatome 10 may include a blade assembly 40 having a blade 42 and a blade mount 44, where blade 42 has a sharpened blade edge 43. Blade assembly 40 may have a first side 40*a* and a second side 40*b* opposite first side 40*a*, where first side 40*a* may face and/or contact a bottom side or surface 18 of main body 12 when blade assembly 40 is mounted on main body 12, as depicted in FIG. 7. Bottom surface 18 may have a bottom perimeter 19 that therein defines bottom surface 18 and within which blade assembly 40 may be received.

Dermatome 10 may also include a blade protector or guard 50 capable of connecting to blade assembly 40 and preventing unintended contact with blade edge 43. Unintended contact with blade edge 43 may include, but is not limited to, contact with objects other than objects for which blade edge 43 is intended to contact. For example, when dermatome 10 is developed for use in skin graft transplant procedures, unintended contact may include all contact between objects and blade edge 43 other than contact between blade edge 43 and a patch of healthy skin that is to be harvested as a skin graft. Blade guard 50 may have a base 52 configured to face second side 40*b* of blade assembly 40 and a fence 54 that may extend from base 52 in a first direction D'. Fence 54 may take on any shape or size allowing blade guard 50 to connect to blade assembly 40. For example, fence 54 may be configured to address, abut, extend parallel to, or generally cover blade edge 43. In the example, blade edge 43 may have a first contour 20, such as a straight contour, and fence 54 may have a second contour 22, such as a straight contour, where second contour 22 may address first contour 20 when guard 50 is aligned or connected to blade assembly 40.

Figure 1:
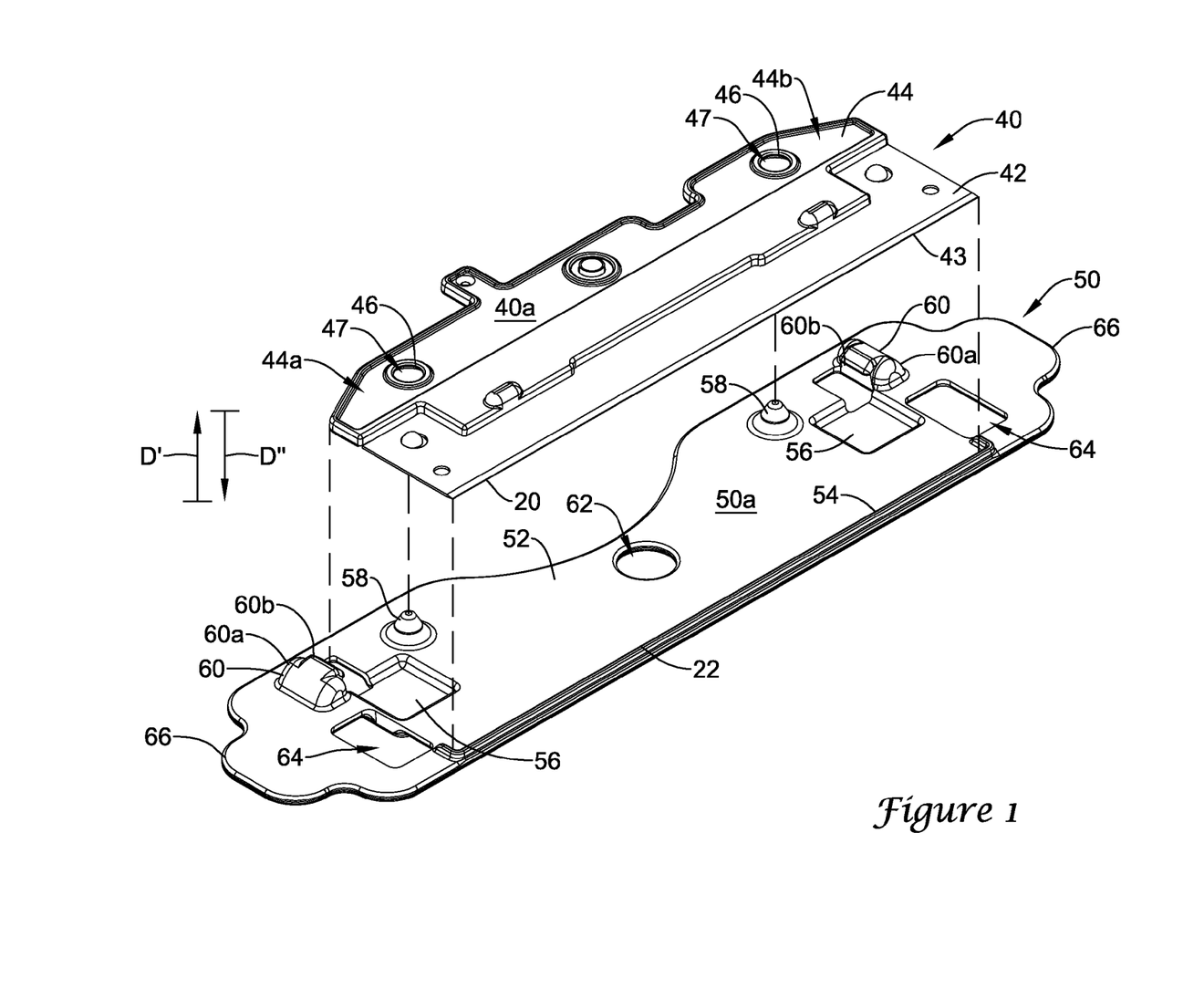
FIG. 1 is an exploded perspective view of blade assembly and guard features of a dermatome according to an aspect of the disclosure.
Figure 2:
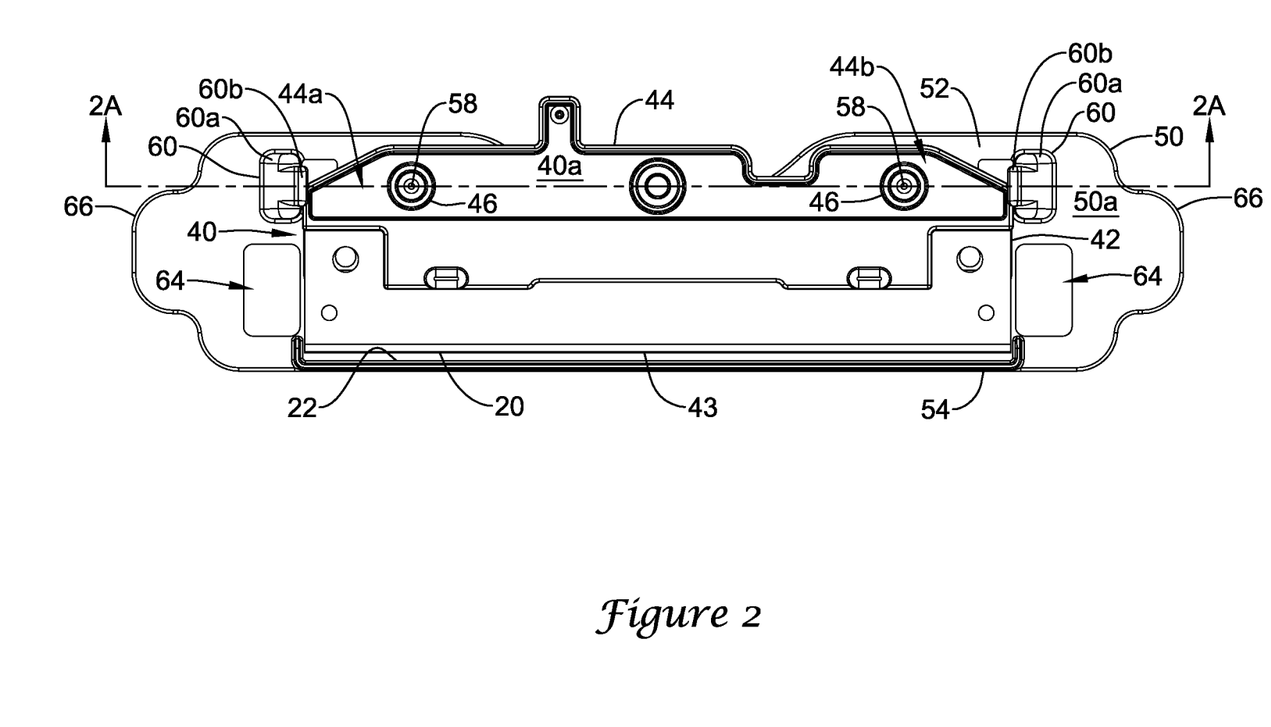
FIG. 2 is a top view of blade assembly and guard features of a dermatome according to an aspect of the disclosure.
Figure 4:
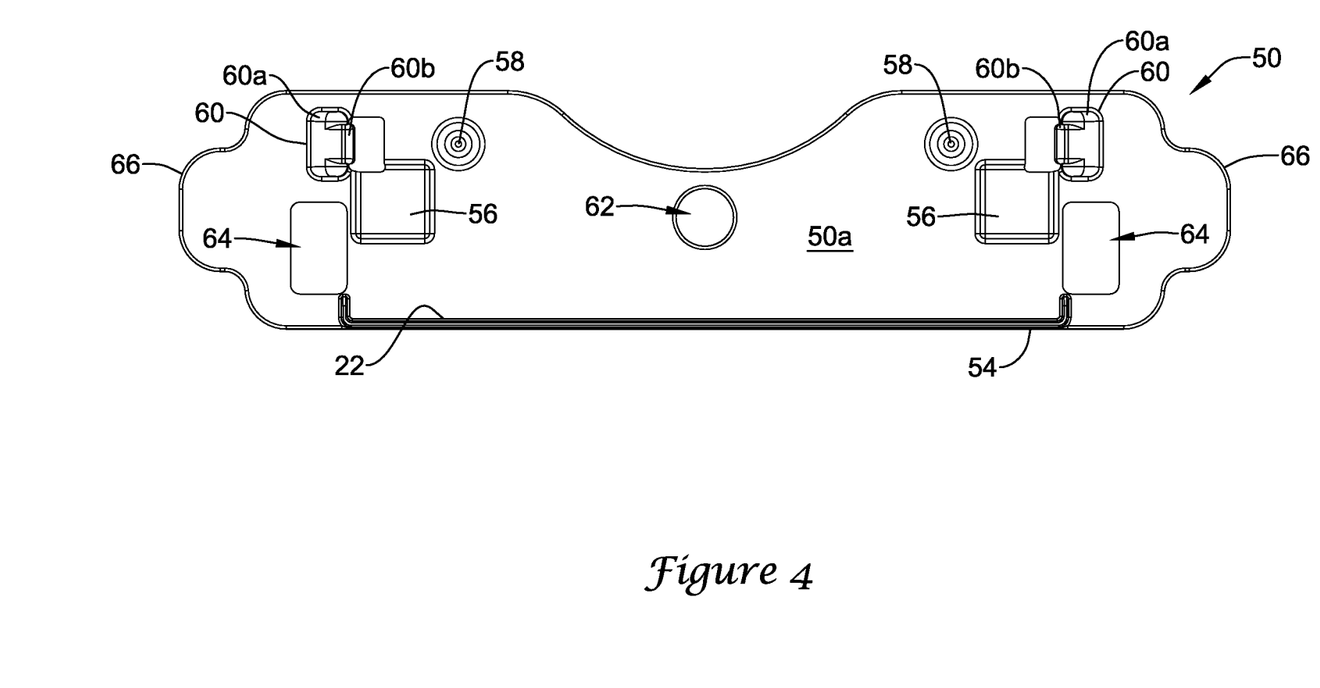
FIG. 4 is a top view of guard features of a dermatome according to an aspect of the disclosure.
Figure 5:
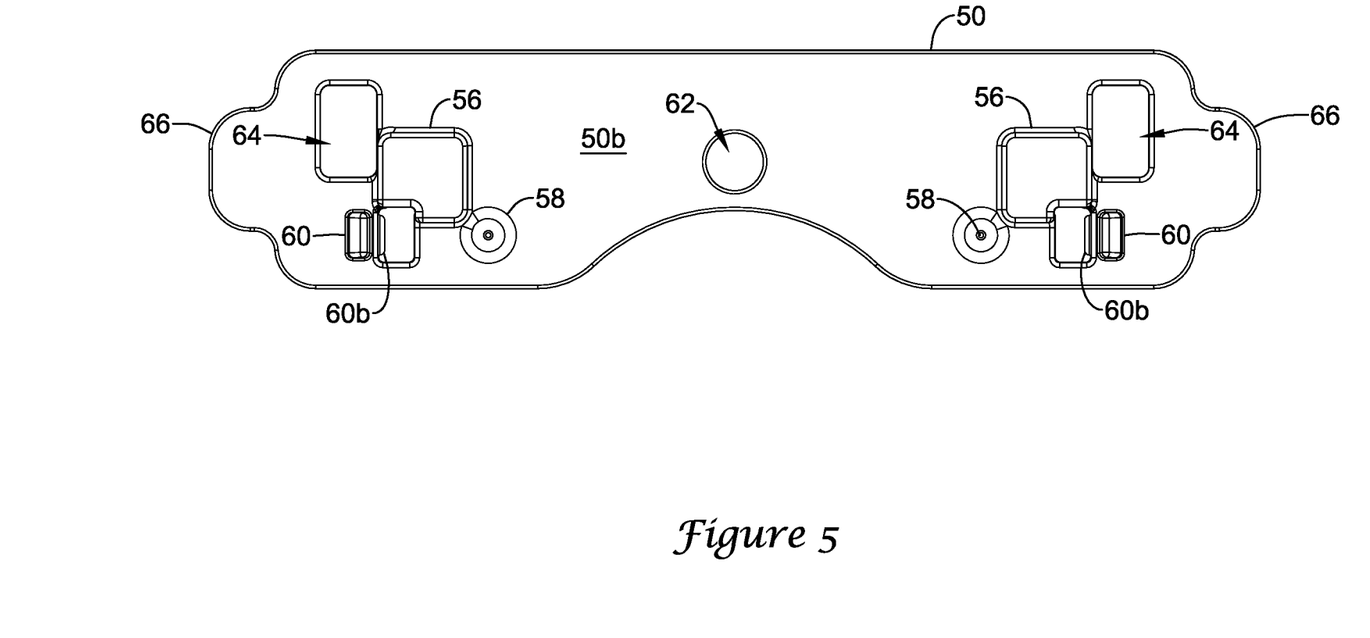
FIG. 5 is a bottom view of the guard features depicted in FIG. 4.

Blade guard 50 may also include at least one locator 58 extending from base 52 in first direction D', as seen in FIGS. 1, 2 and 4. Locator(s) 58 may be blade assembly locators 58 and may be any shape or size. For example, locator 58 may be a shape and size capable of orienting blade guard 50 with respect to blade assembly 40. Moreover, and in the example, locator 58 may take on any shape or size capable of at least engaging hole(s) 47 of guard locator 46. Thus, blade assembly locator 58 may be a protrusion or detent extending from base 52 in first direction D', where the protrusion or detent is capable of engaging hole(s) 47. As seen in FIGS. 1, 2 and 4, locator 58 may be pointed, cone-shaped or frustoconical or other shaped protrusions extending in first direction D'. In an example where multiple protrusions are utilized for blade assembly locator 58, the protrusions may be located at any location along base 52 that correspond to respective holes 47 of blade guard locator 46 while blade assembly 40 and blade guard 50 are properly aligned or connected.

Blade guard locator 46 may be at least partially defined by blade assembly 40. Guard locator 46 may take on any shape and size. For example, as depicted in FIGS. 1, 2 and 7, guard locator 46 may have at least one hole 47, where hole(s) 47 may be at least partially defined by blade mount 44 and may extend from second side 40*b* toward and/or to first side 40*a*. In the example, hole(s) 47 may be configured to engage or receive blade assembly locator(s) 58.

As seen in FIGS. 1, 2, 4 and 7, blade guard 50 may include at least one connector 60. Connector(s) 60 may extend from base 52 in first direction D' and may be any shape or size capable of connecting to blade assembly 40. For example, connector(s) 60 may have an extension 60*a* extending perpendicularly from base 52 to a top 60*b* extending perpendicularly from extension 60*a* and in the direction of blade assembly 40. Connector(s) 60 may be snap connectors or any other connecting mechanism. Connector(s) 60 may be configured to connect to blade assembly 40 by any means. For example, connector(s) 60 may be connected to blade assembly 40 through a snap connection; that is, connector(s) 60 may bend to allow blade assembly 40 to be pressed into blade guard 50 (or connector(s) 60 pressed onto blade assembly 40) and then connector(s) 60 may bend back to, or near, an original position, where top 60*b* may engage first side 40*a* of blade assembly 40. Alternatively or in addition, blade assembly 40 may connect to guard 50 through a slide connection or any other type of connection. For example, blade assembly 40 may slide into connectors 60 while base 52 of guard 50 is bent or deflected such that guard 50 may be capable of receiving a stake or button 48 extending toward guard 50 from blade assembly 40 in a receiving hole 62 on base 52 and blade assembly 40 may engage connectors 60. In the example, once assembly 40 engages guard 50, base 52 of guard 50 may return to, or near, an original configuration. In general, removing guard 50 from a connection with blade assembly 40 may be accomplished by reversing the connection steps or through another technique or process.

Figure 2A:
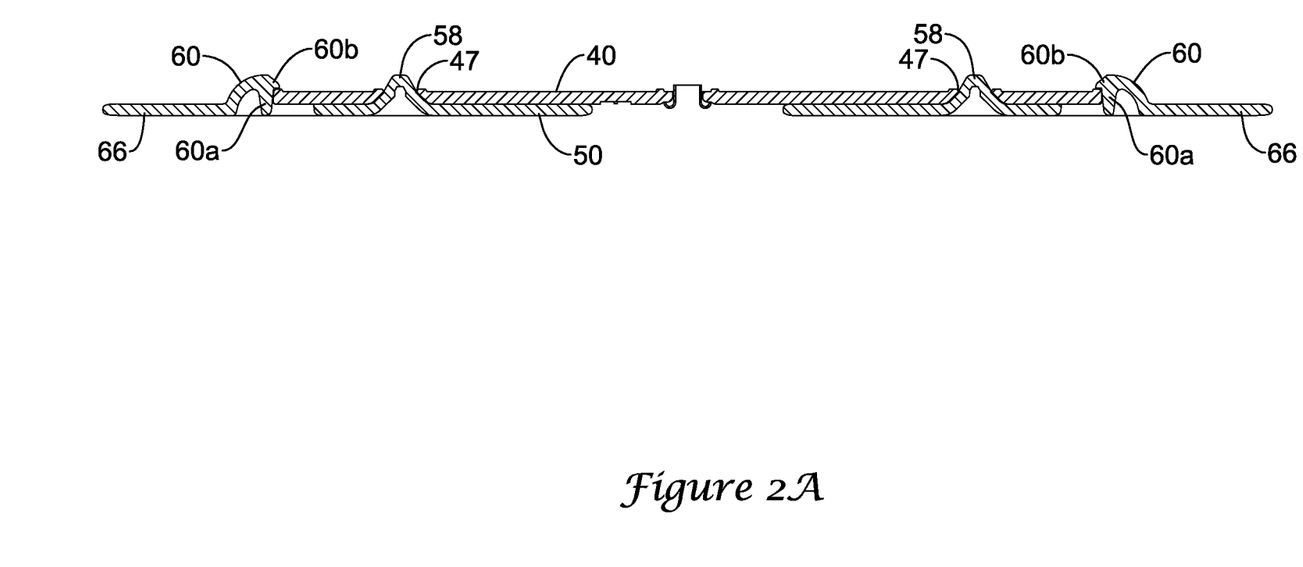
FIG. 2A is a cross-sectional view taken along line 2A-2A of FIG. 2.

As seen in the cross-sectional view of FIG. 2A, connectors 60 may be configured such that extensions 60*a* may be positioned facing and/or abutting, or otherwise adjacent to side edges of blade assembly 40 with tops 60*b* of connectors 60 forming lips positioned on, facing, and/or abutting first side 40*a* of blade assembly 40, while base 52 of blade guard 50 is facing and/or abutting second side 40*b* of blade assembly 40. Thus, connectors 60 may extend from first side 50*a*, which is facing second side 40*b* of blade assembly 40, around side edges of blade assembly 40 and engage first side 40*a* of blade assembly 40 to detachably couple blade guard 50 to blade assembly 40.

Also shown in FIG. 2A are blade assembly locators 58 (e.g., projections) of blade guard 50 extending into blade guard locators 46 (e.g., holes 47) from first side 50*a* of base 52 of blade guard 50 facing second side 40*b* of blade assembly 40.

Figure 3:
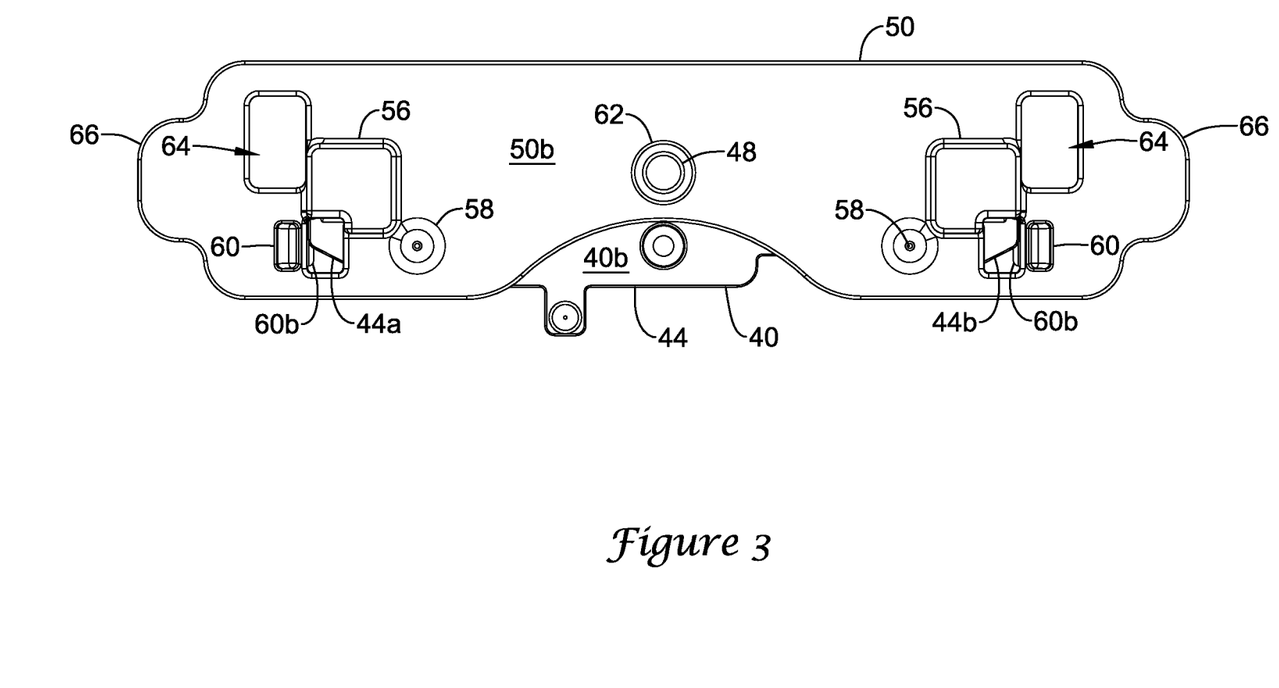
FIG. 3 is a bottom view of the blade assembly and guard features depicted in FIG. 2.

Blade guard 50 may include stake receiving hole 62 extending through base 52. Hole 62 may be at least partially defined by base 52 of guard 50 and capable of receiving a button or stake 48 extending from blade assembly 40 in a second direction D". Hole 62 may be positioned at any location on base 52 so as to be aligned with and configured to receive button or stake 48 extending from blade assembly 40. As depicted in FIGS. 1 and 3-7, hole 62 may be located substantially equidistant from connectors 60 or blade assembly locators 58, or both. Button or stake 48 may extend from blade assembly 40 toward blade guard 50 and blade guard 50 may be configured to receive stake 48 in stake receiving hole 62. Stake 48 may be utilized to make a permanent connection between blade 42 and blade mount 44 or it may be used for any other purpose or even excluded. Stake 48 may be positioned at any location along second side 40*b* of blade assembly 40 so as to be aligned with and configured to extend into and at least partially through hole 62 of blade guard 50. In the event stake or button 48 is excluded, hole 62 may be excluded or modified to accommodate a different mechanism connecting blade 42 and blade mount 44. As depicted in FIGS. 3, 6 and 7, for example, stake 48 may be located substantially equidistant from blade guard locators 46.

As depicted in FIGS. 1-7, blade guard 50 may include capture hole(s) or opening(s) 64. Captures opening(s) 64 may receive plate capture(s) 24 extending from main body 12, where capture(s) 24 may be positioned at any location of main body 12 and may extend from bottom surface 18 in second direction D" toward blade assembly 40 and guard 50. Capture opening(s) 64 may be at least partially defined by base 52. For example, capture opening 64 may be a hole extending through guard 50 from a first side 50*a* of base 52 to a second side 50b of base 52. Opening(s) 64 may be any size or shape capable of receiving plate capture(s) 24 therethrough. For example, as seen in FIGS. 1-7, capture opening(s) 64 may have a rectangular shape. Captures opening(s) 64 may be positioned on or in guard 50 at any location aligned with capture(s) 24. For example, the location of capture openings 64 on or in guard 50 may be dictated by the location of captures 24 extending from main body 12 or the location of captures 24 may be dictated by the location of the capture openings 64. There may be as many capture openings 64 as needed to receive capture(s) 24 and to allow guard 50 to remain connected to blade assembly 40 after blade assembly 40 has been mounted to or on bottom surface 18 of main body 12.

As seen in FIGS. 1-7, blade guard 50 may include wings or tabs 66 extending beyond the lateral extents of blade assembly 40. Tabs 66 may be formed integrally with base 52 or tabs 66 may be extensions extending from opposing ends of base 52. In an illustrative aspect, tabs 66 may be integrally formed with base 52 and may be substantially planar with first side 50a and second side 50b of base 52. In the example, when tabs are integrally formed from base 52, capture openings 64, connectors 60 and blade assembly locators 58 may overlap with or extend onto tabs 66.

Blade guard 50, as depicted in FIGS. 1, 3 and 7, may include hole(s) or indent(s) 56 for receiving blade locator(s) 45 of blade assembly 40. As seen in FIG. 7, blade assembly 40 may include blade locators 45 that extend from blade mount 44. Blade locators 40 may be positioned at any location along blade assembly 40. For example, two blade locators 45 may extend from blade mount 44, where a first blade locator 45a extends from a first end 44a of blade mount 44 toward blade 42 and a second locator 45b extends from a second end 44b of blade assembly 44 toward blade 42. Blade guard 50 may have indents 56 corresponding to locators 45, where indents 56 may be able to receive blade locators 45. Indents 56 may allow for a close fitting between guard 50 and blade assembly 40.

Connected guard 50 and blade assembly 40 may be mounted on main body 12 such that blade assembly 40 is placed substantially within bottom perimeter 19 and guard 50 extends within and outside of perimeter 19, where tabs 66 are positioned at least partially outside of perimeter 19. Tabs 66 may extend outside of perimeter 19 for any purpose. For example, tabs 66 may extend outside perimeter 19 to facilitate removing guard 50 from its connection with blade assembly 40 after placing blade assembly 40 in or on main body 12. In the example, when tabs 66 extend outside of perimeter 19, a force may be applied to tabs 66 in the general second direction D", which may bend base 52 and connector(s) 60 and may cause connector(s) 60 to disconnect from first side 40a of blade assembly. The method of utilizing tabs 66 to remove guard 50 from blade assembly 40 may allow blade guard 50 to be peeled from the connection with blade assembly 40. Alternatively or in addition, tabs 66 may be utilized to remove guard 50 from blade assembly 40 through a sliding technique. For example, a force may be applied to tabs 66 in the general first direction D' or by squeezing tabs 66 toward a center of base 50 and in the first direction D' in order to deflect or bend base 52 to leave a clearance between first side 50a of guard 50 and button or stake 48. In the example, after the clearance is formed between button 48 and guard 50, guard 50 may be slid from engagement with blade assembly 40. In similar, but generally reversed techniques, tabs 66 may also assist in applying guard 50 to a mounted blade assembly 40 in order to remove a previously mounted blade assembly 40 from dermatome 10.

Figure 9:
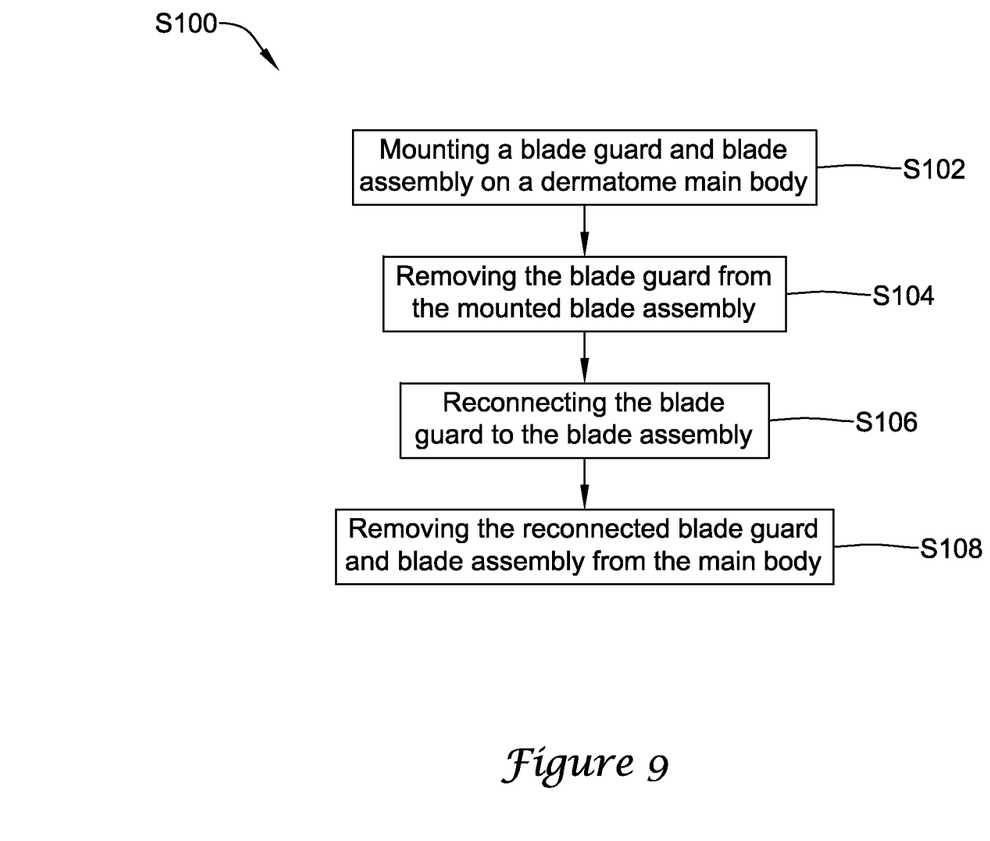
FIG. 9 is a flow diagram of steps for an assembly of a dermatome according to an aspect of the disclosure.

A method of operation S100, as depicted in FIG. 9, may have a first step S102 where blade guard 50 and blade assembly 40 (which have been previously assembled together) may be mounted on bottom surface 18 of main body 12. Assembly 40 and guard 50 may be considered to be mounted once blade assembly 40 is in stable contact with main body 12, whether there is a further connection or not. Blade guard 50 and blade assembly 40 may be connected prior to packaging or a user may connect blade assembly 40 to blade guard 50 prior to handling if guard 50 and assembly 40 are received separately. After mounting blade assembly 40 and guard 50 on main body 12, blade guard 50 may be removed or separated from blade assembly 40 and main body 12 in a second step S104. Blade guard 50 may be removed from blade assembly 40 by any removal technique. For example, a pressure in second direction D" may be applied to first side 50a of guard 50 at or near tab(s) 66. If more than a single tab 66 is utilized, pressure in second direction D" may be applied to one or more tabs 66. Pressure applied to tab(s) 66 may cause guard 50 to bend at one or more positions between connector(s) 60. The bending of guard 50 may allow connector(s) to disconnect or release from first side 40a of blade assembly 40. That is, blade guard 50 may be peeled from mounted blade assembly 40 while being careful not to remove blade assembly 40 from main body 12. Alternatively or in addition, a force may be applied to tabs 66 in the general first direction D' or by squeezing tabs 66 toward a center of base 50 and in the first direction D' in order to deflect or bend base 52 to leave a clearance between first side 50a of guard 50 and button or stake 48, where the clearance may allow for removing guard 50 from assembly 40 by sliding guard 50 from blade assembly 40.

In some instances, once blade guard 50 has been removed from dermatome 10, a user may connect a width plate 30 to dermatome 10 with a fastener 32, as seen in FIG. 8, such that width plate 30 faces second side 40b of blade assembly 40 and main body 12 or has another orientation with respect to blade assembly 50 and main body 12. Width plate 30 may be used to limit the width of a skin graft cut by blade 42 during a medical procedure or for any other purpose. In some instances, after the dermatome 10 has been used in a medical procedure or at any time it is desired to remove blade assembly 40 from dermatome 10, width plate 30 (that is, if width plate 30 was previously applied to dermatome 10) may be removed from dermatome 10 and a user may reconnect blade guard 50 with blade assembly 40 in a third step S106. In step three S106, blade assembly locator 58 extending from first side 50a of blade guard 50 may be aligned with blade guard locator 46. For example, where blade assembly locator 58 is a protrusion extending from first side 50a of blade guard 50 and blade guard locator 46 is a hole 47, blade guard 50 may be aligned with blade assembly 40 by placing blade assembly locator 58 within hole 47 of blade guard locator. After aligning blade guard 50 and blade assembly 40 by aligning locators 46, 58, or during the alignment, plate capture(s) 24 may be fitted within capture opening(s) 64. In addition, fence 54 extending from first side 50a in first direction D' may be positioned proximate blade edge 43 so as to block blade edge 43 from any unintended contact with an object. After or during the aligning and fitting steps, blade guard 50 may be connected or reconnected to blade assembly 40 through the use of connectors 60 extending in first direction D' from base 52. Connector(s) 60 may be forced to bend or flex around blade assembly 40 and connect to or engage first side 40a of blade assembly 40 when the bending or flexing ceases. Alternatively or in addition, blade assembly 40 may be slid into connectors 60 while base 52 of guard 50 is being bent or deflected such that guard 50 may be capable of receiving stake or button 48 extending toward guard 50 from blade assembly 40 in a receiving hole 62 on base 52 and that blade assembly 40 may engage connectors 60. Connector(s) 60 may fasten to first side 40*a* with a snap or slide connection or any other type of connection while first side 50*a* of base 52 of guard 50 faces and/or abuts second side 40*b* of blade assembly 40. The step of reconnecting blade guard 50 to blade assembly 40 may be performed in any manner so long as the result is that blade guard 50 is blocking blade edge 43 after making the connection, where fence 54 addresses blade edge 43 along substantially an entirety of blade edge 43 or at specified intervals or at random intervals as needed to block blade edge 43 from unintended contact with objects.

In fourth step S108, connected or reconnected blade guard 50 and blade assembly 40 may be removed from main body 12. Connected blade guard 50 and blade assembly 40 may be removed from main body 12 by lifting on tab 66 in second direction D" or through any other technique. For example, another technique may include applying a pressure in second direction D" to first side 40*a* of blade assembly 40 by inserting a tool through depressions 14 in main body 12 and contacting first side 40*a*. As blade edge 43 is guarded or blocked by fence 54, a user or object will not come into any unintended contact with blade edge 43 during mounting or removal of blade edge from dermatome 10. In addition, blade assembly 40 may be received and/or disposed of with blade guard 50 attached thereto, which further prevents any unintended contact with blade edge 43 prior to using blade assembly 40 with dermatome 10 or after blade assembly 40 is removed from dermatome 10.

The disclosed device and methods of using eliminate direct handling of an exposed blade edge 43 both before inserting the blade assembly 40 into dermatome 10 and when removing the inserted blade assembly 40 from dermatome 10. The protector or guard 50 device protects the blade edge 43 during sterilization, transportation, storage, insertion, removal and blade disposal. That is, the disclosed device allows the blade guard or protector 50 to stay attached to blade assembly 40 during handling and only needs to be removed after the blade assembly 40 has been correctly inserted into the dermatome device. Blade protector or guard 50 can be placed back over blade assembly 40 on main body 12 after blade assembly 40 is no longer needed and prior to its removal from main body 12. The attached blade protector or guard 50 may be disposed of with a spent or used blade assembly 40.

Those skilled in the art will recognize that the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. An assembly for a dermatome comprising:
   a blade assembly having a first side and a second side, the blade assembly including:
      a sharpened blade edge;
   a blade guard including:
      a base configured to face the second side of the blade assembly;
      a fence extending from the base in a first direction, the fence configured to cover the sharpened blade edge;
      at least one locator extending from the base in the first direction and configured to orient the blade guard with respect to the blade assembly;
      first and second connectors each having a first portion extending from the base in the first direction and a second portion extending from the first portion in a direction toward the blade assembly to engage the blade assembly; and
      first and second tabs extending from first and second ends of the blade guard and extending laterally beyond the first and second connectors in directions substantially opposite the direction in which the second portion of the first and second connectors extends to engage the blade assembly.

2. The assembly of claim 1, wherein the first and second connectors are configured to extend around opposing lateral edges of the blade assembly to couple the blade guard to the blade assembly with the base facing the second side of the blade assembly while portions of the first and second connectors contact the first side of the blade assembly.

3. The assembly of claim 2, wherein the first and second tabs extend beyond the opposing lateral edges of the blade assembly.

4. The assembly of claim 3, wherein the locator includes first and second protrusions extending from the base in the first direction, and the blade assembly includes a pair of openings configured to receive the first and second protrusions therein to orient the blade guard with the blade assembly.

5. The assembly of claim 1, wherein the blade assembly includes a guard locator, and
   wherein the at least one locator of the blade guard includes a blade assembly locator configured to engage the guard locator.

6. The assembly of claim 5, wherein the guard locator is a hole; and
   wherein the blade assembly locator is a protrusion extending from the base of the blade guard in the first direction configured to be received in the hole of the blade assembly.

7. The assembly of claim 1, wherein the first and second connectors are snaps configured to engage the first side of the blade assembly with the base facing the second side of the blade assembly.

8. The assembly of claim 1, wherein the blade assembly includes a stake extending from the second side, and
   wherein the blade guard is configured to receive the stake.

9. The assembly of claim 8, wherein the blade guard receives the stake in an opening at least partially defined by the base.

10. A dermatome system, comprising:
    a main body including:
       a plate capture extending from a surface of the main body, the plate capture configured to receive a removal bottom plate;
    a blade assembly including:
       a blade having a sharpened blade edge; and
       a blade mount having a guard locator;
    a blade guard including:
       a blade assembly locator configured to engage the guard locator of the blade mount;
       a fence configured to protect the sharpened blade edge;
       a capture opening configured to receive the plate capture of the main body therein such that the blade assembly is positionable onto the main body with the blade guard attached to the blade assembly;
       a connector extending in a direction toward a center of the blade assembly for connecting the blade guard to the blade assembly; and at least one tab extending laterally beyond the connector in a direction substantially opposite the direction the connector extends toward the center of the blade assembly.

11. The dermatome system of claim 10, wherein the blade guard includes a base, and
wherein the blade assembly locator and the fence extend from the base and extend in a first direction.

12. The dermatome system of claim 11, wherein the base at least partially defines the capture opening.

13. The dermatome system of claim 12, wherein the plate capture extends from the main body in a second direction and configured to be received in the capture opening.

14. The dermatome system of claim 11, wherein the connector extends from the base in the first direction.

15. The dermatome system of claim 14, wherein the blade assembly has a first side and a second side opposite the first side, and
wherein the base abuts the second side of the blade assembly and the connector engages the first side of the blade assembly.

16. The dermatome system of claim 14, wherein the connector creates a snap connection with the blade assembly.

17. The dermatome system of claim 11, wherein the main body has a bottom perimeter within which the main body is configured to receive the blade assembly, and
wherein the at least one tab extends beyond the bottom perimeter of the main body.

* * * * *